United States Patent [19]

Wardle

[11] Patent Number: 4,745,908
[45] Date of Patent: May 24, 1988

[54] INSPECTION INSTRUMENT FEXIBLE SHAFT HAVING DEFLECTION COMPENSATION MEANS

[75] Inventor: John L. Wardle, Shelton, Conn.

[73] Assignee: Circon Corporation, Santa Barbara, Calif.

[21] Appl. No.: 47,750

[22] Filed: May 8, 1987

[51] Int. Cl.[4] .............................................. A61B 1/06
[52] U.S. Cl. .......................................... 128/6; 128/4; 138/120
[58] Field of Search ................ 128/3, 4, 5, 6, 7; 350/96.26; 138/120

[56] References Cited

U.S. PATENT DOCUMENTS

| | | | |
|---|---|---|---|
| 1,958,656 | 5/1934 | Buerger | 128/7 |
| 2,120,996 | 6/1938 | Wappler | 128/7 |
| 3,368,552 | 2/1968 | Bottcher | 128/4 |
| 3,610,231 | 10/1971 | Takahashi et al. | 128/6 |
| 3,792,701 | 2/1974 | Kloz et al. | 128/7 |
| 3,918,438 | 11/1975 | Hayamizu et al. | 128/4 |
| 4,530,568 | 7/1985 | Haduch et al. | 128/6 X |
| 4,616,631 | 10/1986 | Takahashi | 128/6 |

Primary Examiner—William H. Grieb
Attorney, Agent, or Firm—Perman & Green

[57] ABSTRACT

An inspection instrument for accessing a target area has a shaft with a structural core of flexible material. The core has sufficient rigidity to provide a continuous frame for the shaft, but also allows the shaft to be flexible for deflection. The core has a conduit means which passes through the core along a non-straight path to act as a deflection compensation means for conduit means deformation during shaft bending or deflection.

18 Claims, 3 Drawing Sheets

INSPECTION INSTRUMENT FEXIBLE SHAFT HAVING DEFLECTION COMPENSATION MEANS

BACKGROUND OF THE INVENTION

1. Field of the Invention

This invention relates to flexible inspection instruments for use in both industrial and medical applications and, more particularly, to an elongated, flexible, fiberscopic inspection device with a substantially flexible shaft having a channel means therewith and a deflection compensation means.

2. Prior Art

Elongated tubular inspection devices, particularly such devices incorporating flexible fiber-optics, are often used to inspect sites which would not normally be visible to the human eye. One application of such tubular inspection devices is in the practice of medicine. For instance, a common form of such device, known as a flexible ureteropyeloscope, is used for the inspection of the human ureter and entire kidney area while a similarly structured device, known as a colonoscope, is used for the inspection of the colon.

The ureteropyeloscope is conventionally used for a variety of functions such as observation of areas and presenting a working tool at the area for such things as removing ureteral or kidney stones, dislodgement or electro-hydraulic destruction of ureteral stones, taking biopsies, irradiating tumors with laser fibers, etc. The ureteropyeloscope examination can involve the physician's placing the instrument in the body through the urethra, then into the bladder, then through one of the ureteral tubes and then, if necessary, into the kidney itself. This is usually a time consuming and potentially tortuous path through several organs of the body.

The inspection instrument generally has a control head forming a proximal end and a flexible tubular shaft, the end of which forming a distal end. The physician observes target areas through an eyepiece in the control head. Generally, the ureteropycloscope is provided with a bundle or bundles of optical fibers which bring light to its objective end, the end which is placed adjacent the area to be examined, and a bundle or bundles of light transmitting fibers through which an image of the examined area is transmitted back to the eyepiece. The ureteropyeloscope can generally further incorporate a channel which provides a conduit for providing washing fluid to the site under examination as well as for the introduction of accessory devices to the site such as a biopsy forceps.

The flexible tubular shaft extending between the proximal end and the distal end of the flexible instrument generally has a variety of components passing therethrough. The shaft may have such components as a fiber bundle, a working channel and distal end control wires. The tubular shafts can also have a variety of cross sectional shapes as is seen from U.S. Pats. Nos. 1,958,656; 2,120,996; 3,368,552; 3,792,701 and 3,918,438.

The control head of a flexible ureteropyeloscope is generally capable of serving many purposes including housing the optical eyepiece assembly, providing an entry for a light carrier from a light source, housing a deflection control system for controllably moving the distal end and providing an entry for tools and fluids to enter into the control head and be transported to the objective end by means of the working channel. One such control head is described in co-pending U.S. Patent Application Ser. No. 07/017,813 filed Feb. 24, 1987 entitled "Improved Instrument Control Head" by the same inventor and having the same assignee as the present application, which is incorporated by reference in its entirety herein.

One type of deflectable flexible inspection instrument is described in U.S. Pat. No. 4,530,568 by Haduch et al. entitled "Flexible Optical Inspection System" assigned to the same assignee as herein. In the instrument in that patent, ribs or vertebrae 54 and 55 are used to impart limited flexibility and sufficient rigidity to the instrument to provide a structure which is deflectable. However, use of instruments which require ribs for structural integrity cannot be made with relatively small cross-sectional shafts and therefore have a practical limit on the smallness of their cross-sectional area. In addition, deflectable instruments which use a rib-like frame in their shafts also require protective sheaths around their fiber-optics bundles and control cables which further increases the cross-sectional size of their shafts.

Another type of flexible inspection instrument is shown in U.S. Pat. No. 4,616,631 of Takahashi, which generally has a core of a relatively flexible material also known as a multi-lumen core. The core has straight conduits for housing such things as fiber-optic bundles or allowing the passage of instruments or fluids to the distal end. However, these instruments do not have controllable deflection distal ends because a deflection means contained in the straight conduit of a flexible core has a tendency to involuntarily move the distal end of the instrument during bending of the core or twisting or torquing of the shaft once a target area has been reached.

A problem arises in using presently available inspection instruments in that rib-like framed or multi-sheath framed shafts can often be too large to access target areas through relatively small channels.

A further problem arises in using presently available inspection instruments in that shafts that use flexible cores do not have a deflection means for controllably deflecting the distal end without involuntary movement during bending or torquing of the shaft.

A further problem arises in using presently available inspection instruments in that shafts that use flexible cores do not have a means for compensating for shaft deflection which causes channel means deformation.

SUMMARY OF THE INVENTION

The foregoing problems are overcome and other advantages are provided by an instrument of a generally tubular flexible shape for accessing a target area, The instrument has a shaft having a channel means and a deflection compensation means.

In accordance with one embodiment of the invention, the instrument comprises a control head forming a proximal end, an objective head forming a distal end and a tubular flexible shaft therebetween. The shaft comprises a structural core made of a flexible material having a first longitudinal axis and a conduit means therewith. The conduit means is, at least partially, offset from the first longitudinal axis such that the core has a first pre-determined length and the conduit means has a second pre-determined length.

In a preferred embodiment, the shaft comprises a distal end deflection means located in the conduit means for controllably deflecting the digital end of the instrument. The deflection means is contained between the objective head and the control head in a non-straight path and has a length between the objective head and the control head greater than the length of the shaft. Also located with the conduit means, are two bundles of light transmitting fibers which transmit light between the control head and the objective head. A shaft torque stabilizer means may also be provided such as a wire braid sheath. This sheath may be selectively connected to the core to allow for proper column strength and deflection agility in the shaft.

In yet another embodiment, the core is an extruded polymer material having a first longitudinal axis with a channel means offset, at least partially, from said first longitudinal axis. The core is twisted about the first longitudinal axis to thereby spiral the channel means. A suitable twist retention means is connected to the core to maintain the twist. A distal end deflection means can be positioned with the channel means.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
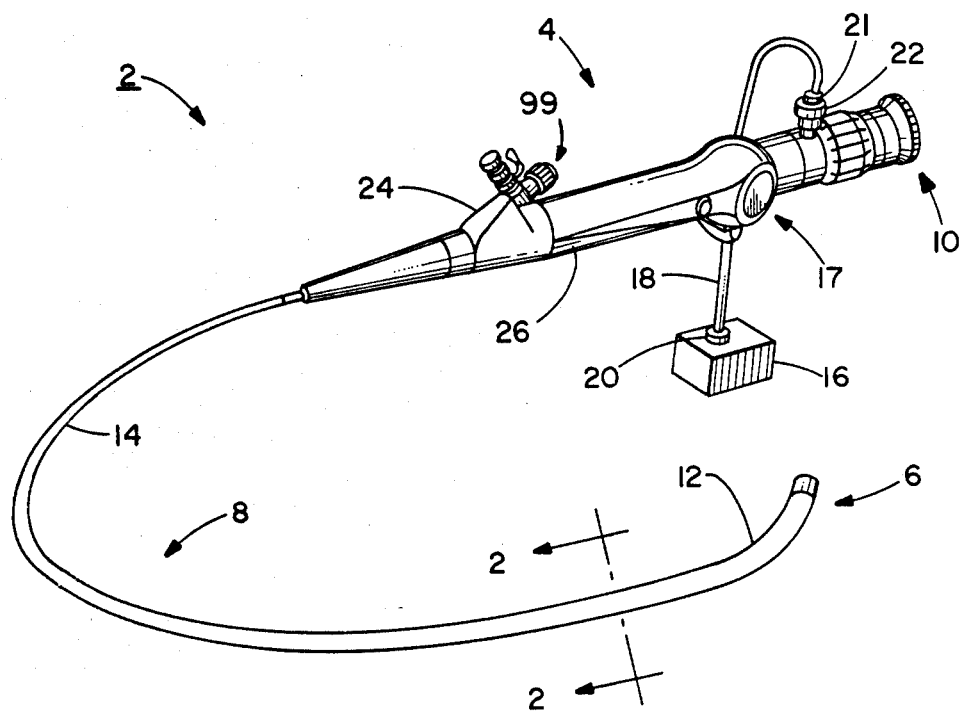
FIG. 1 is a perspective view of a flexible inspection instrument incorporating features of the present invention.

Referring to FIG. 1, there is shown one embodiment of a flexible inspection instrument 2, incorporating features of the invention. The inspection instrument 2, in this embodiment, is a flexible ureteropyeloscope which is generally for internal examinations and operations on the human body and more particularly for use in the ureter and kidney area of the body. The ureteropyeloscope 2 has a proximal control head 4 having a housing 26, a distal objective head 6 and a tubular flexible shaft 8 interconnecting the control head 4 to the objective head 6.

The tubular flexible shaft 8 is generally capable of conveying the objective head 6 to the site to be examined and is also capable of defining a tubular passage 32 (see FIG. 2) for elongate components extending through the shaft from the control head 4 to the objective head 6. The tubular flexible shaft 8 includes a relatively short distal deflector section 12 connected to the objective head 6 and an extended proximal flexible section 14 between the distal deflector section 12 and the control head 4. The distal deflector section 12, in this embodiment, is adjustable in a controlled manner from the control head 4 via a deflection control 17 for manipulating the objective head 6 over the entire site, such as a body cavity, being examined and to this end has a high degree of flexibility. The flexible shaft section 14, however, can be less flexible, being required to flex only sufficiently to follow the contours of the canal or tract leading to the target area.

For inspecting the site to be examined, in this embodiment, the ureteropyeloscope has an optical system including an external light carrier or bundle of light transmitting fibers 18 for carrying light from a lamp box or light source 16 for illuminating the inspection site. Light carrier 18 is connected to the lamp box 16 by lamp box connector 20. In the embodiment shown the carrier 18 has a control head connector 21 which connects to a rotatable combination light post/vent valve assembly 22 on the control head 4. A first light carrier 44 (see FIG. 2) is located in the instrument 2 and receives light from the external light carrier 18 at the light post/vent valve assembly 22. The first internal light carrier 44 travels through the control head 4 and through the flexible shaft 8 to the objective head 6. The carrier 44 then provides light to the inspection site. A light image received from the illuminated site is conveyed back to an eyepiece assembly 10 by a second internal light carrier 46 (see FIG. 2) and suitable optical system, (not shown). Using the eyepiece assembly 10 the physician or clinician can view the operative field and follow the movement or the distal end of the flexible shaft relative to the operative field. The accessory passage or working channel 32 (see FIG. 2) extends from the control head 4 through the flexible shaft 8 to terminate in an open end in the objective head 6 and is accessible through an entry port 99 in a rotatable entry block 24 mounted on the housing 26 of the control head 4.

Figure 2:
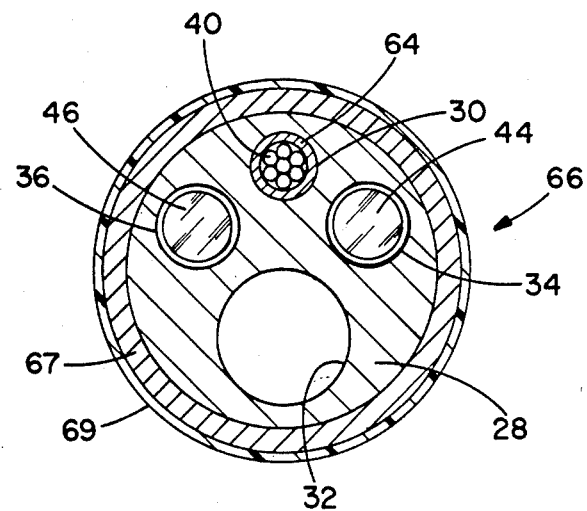
FIG. 2 is a cross-sectional view of the shaft in FIG. 1 taken along line 2—2.

Referring now also to FIG. 2, a cross-sectional view of the shaft 8 of the instrument in FIG. 1 is shown. In the embodiment shown, the shaft 8 has a single structural core 28 made of a flexible material which travels substantially the entire length of the shaft 8 and is also known as a multi-lumen core. In a preferred embodiment, the core 28 is made of an extruded polymer material such as polyurethane; however, any suitable type of flexible and resilient material can be used. The core 28 generally extends between the control head 4 and the objective head 6. Although flexible and resilient, the core 28 has a longitudinal axis along its length and has sufficient rigidity to establish a flexible structural frame for the shaft 8. Although the core 28 is shown as having a generally circular cross-section, any suitably shaped core can be used. In addition, a core assembly can be made by use of several partial sections of a core which are combined to form the overall core 28.

Located within the core 28, in the embodiment shown, are four conduits or passageways; a deflection conduit 30, a working conduit 32, and two fiber-optic conduits 34 and 36, which travel through the core 28 from a first end 37 (see FIG. 3) of the core 28 adjacent the control head 4 to a second end 38 (see FIG. 3) of the core 28 adjacent the objective head 6. The conduits 30, 32, 34, 36 are substantially continuous between the two ends 37 and 38 of the core 28; however, some of their paths may be either straight, curved or even have a specific pattern. The deflection conduit 30 is generally provided as a housing conduit for housing a deflection means. Located within the deflection conduit 30, in this embodiment, is a deflection member 40, such as a cable or wire, coaxially mounted within a spring sheath 64. The operation of the deflection means of this embodiment is generally disclosed in co-pending U.S. Patent Application entitled "Multi-Lumen Core Deflecting Endoscope" by Wardle, Ser. No. 07/047,687 filed May 7, 1987, assigned to the same assignee as the present application, which is incorporated by reference in its entirety herein. However, any suitable type of deflection means could be used.

The working conduit 32 is generally provided as the accessory passage or working channel for the instrument 2. The working channel 32 is connected at one end to the entry port 99 in the rotatable entry block 24 (see FIG. 1) at the first end 37 of the core with the opposite end of the working channel 32 being connected at the second end 38 of the core 28 to a working channel conduit (not shown) in the objective head 6. The working conduit 32 of the core 28 thus is capable of allowing fluids and instruments introduced at the control head 4 to pass through the flexible shaft 8 and exit the objective head 6 to access the target area.

The two fiber-optic conduits 34 and 36 are generally provided to house the two light carriers or bundles of light transmitting fibers 44 and 46. In the alternative, a single light bundle could be used in the instrument 2 or alternatively, any number of bundles. As described above, the first light carrier 44 receives light from the external light carrier 18 at the light post/vent valve assembly 22. The first light carrier 44 travels through the control head 4 and through the conduit 34 of the core 28 to the objective head 6. The carrier 44 can thus provide light to the inspection site. A light image received from the illuminated site is conveyed back to the eyepieces assembly 10 by the second internal light carrier 46 which travels from the objective head 6 through the conduit 36 and control head 4 to the assembly 10. In a preferred embodiment the carriers 44 and 46 are substantially free to move within the conduits 34 and 36 and due to the fact that the core is made of a flexible material, the light carriers can be contained in the conduits 34 and 36 without an additional protective sheath between the carriers 44 and 46 and the core 28. This can clearly help to reduce the cross-sectional size of the shaft 8. Although the core 28 has been described as having four internal conduits, other embodiments may include more or fewer conduits in addition to alternatively having the conduits located externally on the core 28.

As shown in the embodiment of FIG. 2, the core 28 has an exterior cover 66. The cover 66, in this embodiment, comprises a wire braid sheath 67 having an additional covering 69 of a flexible and resilient material, such as polymer material. The wire braid sheath 67 can be made of any suitable material, such as stainless steel, and in this embodiment, helps to provide several functions for the shaft 8.

The braid 67 and covering 69 generally provide the following functions for the shaft 8. First, the wire braid sheath 67 provides a shaft torque stabilizing means to maintain a registry between the control head 4 and the objective head 6 in the event that the instrument must be twisted or torqued during insertion to a target area or alternatively to turn the objective head once the target area has been reached to allow for proper deflection of the distal end. Second, the additional covering 69 of polymer material provides a smooth surface for cooperative passage through channels such as channels in the human body. Third, the sheath cover 66 protects the flexible core 28 from externally caused damage that might occur through normal use and storage of the instrument. Fourth, the braid 67 can be connected to the core 2B to increase column or shaft strength over the length of the shaft 8.

In a preferred embodiment, the wire braid sheath 67 is selectively connected to the core 28 by means such as bonding by adhesive; however, any suitable connection means could be used. To provide for non-interference from the braid 67 during deflection of the distal end, the braid 67 is preferably not bonded to the core 28 adjacent the distal region of the shaft 8. Because the braid 67 is bonded selectively to the core 28, the braid 67 can also restrict the flexibility of the shaft, at least partially. However, this reduced flexibility does not affect the distal region of the instrument 2, nor does it substantially interfere with the instrument's ability to navigate through tortuous channels. The bonding of the braid 67 to the core 28 stiffens the shaft 8 to give the shaft additional column strength to assist in insertion towards a target area and also prevents buckling. In addition, the outer covering 69 may either comprise a separate cover which is connected to the wire sheath 67 or alternatively the outer cover 69 can be sprayed onto the sheath 67. Alternatively, any type of cover or torque stabilizer means can be used with the core 28 or the core 28 may be used without a sheath cover 66. However, the shaft 8, in the embodiment shown, can have a shaft circumference at least as small as about ten (10) French or a diameter of about 3.33 mils.

Figure 3:
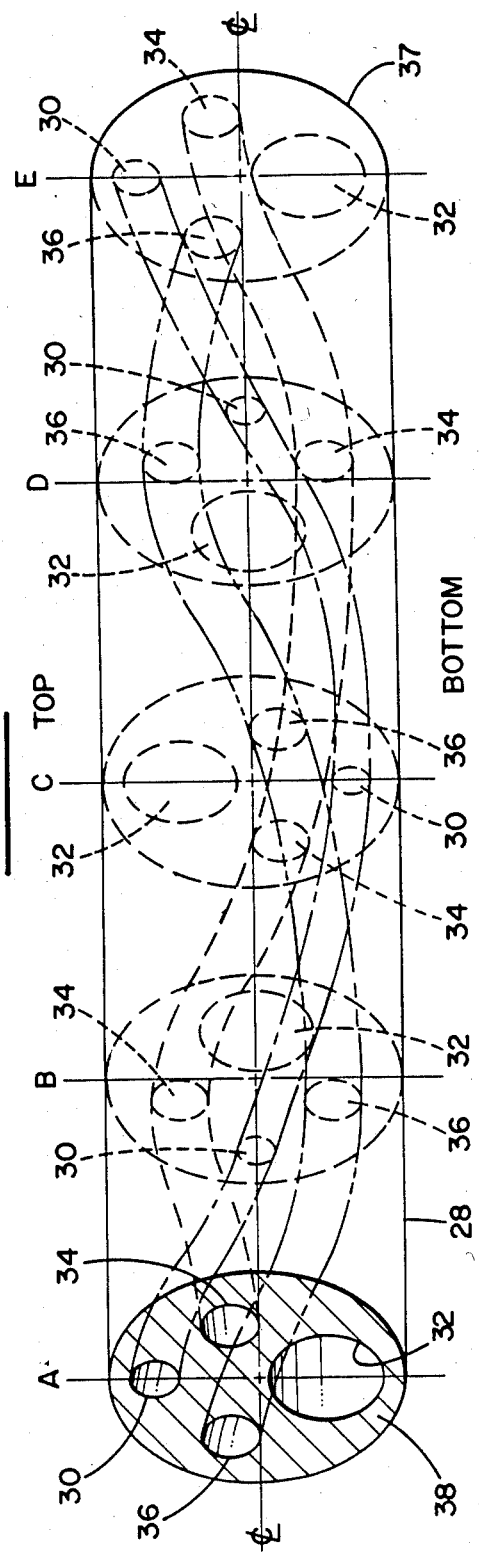
FIG. 3 is a diagrammatical view of the core of FIG. 1 having conduits spiralled along the longitudinal axis.

Referring now to FIG. 3, the core 28 of FIG. 2 will be further described. FIG. 3 shows a diagrammatical view of the core 28 with conduit paths of the conduits 30, 34 and 36 shown. The path of the conduit 32 has been omitted for the sake of clarity only. As illustrated, the conduits 30, 32, 34 and 36 travel through the core 28 between the first end 37 and the second end 38. The conduits 30, 32, 34 and 36 are substantially continuous; however, their paths are not straight. In this embodiment, the paths of the conduits 30, 32, 34 and 36, although maintained in a substantially constant orientation to each other, are spiralled about the core longitudinal axis as they travel from the first end 37 towards a region proximate the second end 38.

Section E of FIG. 3 shows the conduit orientation of the core at the first end 37. As shown in this embodiment, the deflection conduit 30 is located at the top of the core 28 with the working conduit 32 located at the bottom of the core 28. The core 28, in this embodiment, has the conduits 30, 32, 34 and 36 spiralling about the longitudinal axis of the core 28 in a counter-clockwise direction from the first end 37. In an alternative embodiment, the conduits can be spiralled in a clockwise direction.

Section D of FIG. 3 shows the conduit orientation of the core 28 taken along line D in FIG. 3. As shown in this section of the core 28, the four conduits 30, 32, 34 and 36 have retained their orientation relative to each other, but the overall orientation of their position in the core has changed. In this position of the core 28, the conduits have rotated approximately 90 degrees counter-clockwise from their original position at the first end 37 with the fiber-optic conduit 34 on the bottom, the fiber-optic conduit 36 on the top of the core 28 and the deflection conduit 30 and working conduit 32 located on opposing sides of the core 28.

Section C shows the conduit orientation of the core 28 taken along line C in FIG. 3. The conduits 30, 32, 34 and 36 have retained their orientation relative to each other, but once again the overall orientation of their position in the core has changed. In this position of the core 28 the conduits have rotated an additional 90 degrees counter-clockwise from the section at line D with the deflection conduit 30 located on the bottom and the working conduit 32 located on the top. The conduits 30, 32, 34 and 36 continue to rotate as shown in sections B and A in a substantially uniform manner about the longitudinal axis until they reach a region proximate the second end 38 of the core 28. In a preferred embodiment, the conduits are spiralled about the longitudinal axis several times between the first end 37 and a region proximate the second end 38. However, in another embodiment, only the deflection conduit 30 has a spiralled or non-straight path.

The region proximate the second end 38, in this embodiment, is intended for use as the deflection section 12 of the instrument 2. For this reason, it is preferable to have the deflection conduit 30 in a substantially straight position proximate the distal end of the instrument 2 for proper deflection control of the distal end. However, in an alternate embodiment, the paths of the conduits 30, 32, 34 and 36 may be continuously spiralled.

As the figures show, the conduits 30, 32, 34 and 36 change their orientation as the distance from the first end 37 increases. Although the conduits have been described as spiralling about the longitudinal axis of the core 28, they may have any type of path through the core 28 other than purely straight. In addition, the orientation of each conduit relative to each other need not remain constant, but may also vary. Alternatively, more or fewer conduits may be contained in or on the core 28. The number of complete rotations using the spiral method can obviously vary, but in a preferred embodiment the conduits rotate about the longitudinal axis about five times along the length of the core 28.

In a preferred embodiment, the core 28 is fabricated of an extruded polymer material such as polyurethane. However, any suitable material can be used. The core 28 is manufactured with substantially straight conduits therein. To impart the core 28 with a spiralled conduit path, the core 28 is axially twisted about its longitudinal axis. Although the longitudinal axis remains substantially straight, the conduits in the core 28 are spiralled between the first end 37 and the second end 38 as the core 28 is axially twisted.

Because the core 28 can be made of a flexible and resilient material, a twist retention member may optionally be connected to the core 28 to retain its twisted orientation and prevent the core from elastically returning to an untwisted or straight conduit position. Rather than adding an additional twist retention member that might increase the cross-sectional size of the shaft 8, the wire braid sheath 67 of the cover 66 is attached to the core to retain the twist. In a preferred embodiment, the sheath 67 is selectively bonded to the core 28 such that the region proximate the second end 38 of the core can untwist or straighten to allow for proper deflection control. In this embodiment the sheath 67 is bonded to the objective head 6 and selectively to the core 28 by means of an adhesive or the like.

In alternative embodiments, the core 28 can be manufactured without a twist such as by creating the non-straight channels by drilling or as the core is originally extruded. In addition, the core may be fabricated such that deflection conduit 30 is relatively straight, but occupies a relatively large cross-section of the core with the deflection means contained in the conduit 30 in a non-straight manner.

Figure 4:
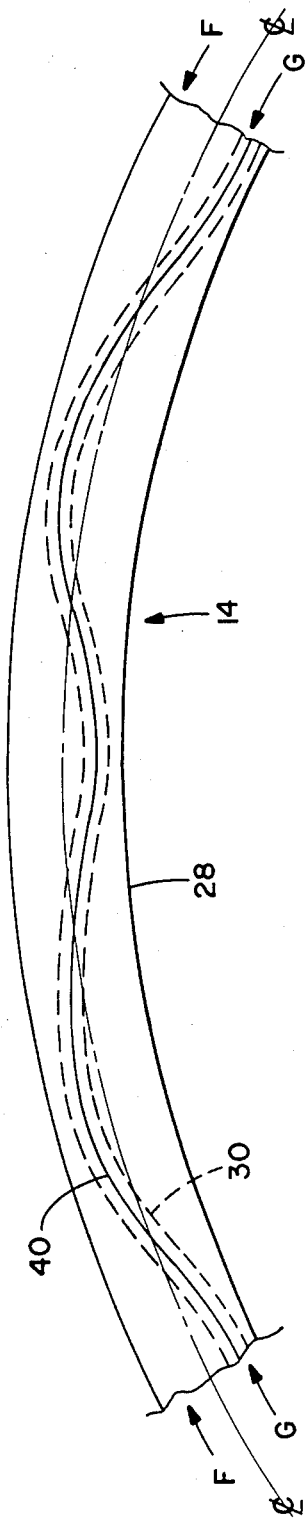
FIG. 4 is a diagrammatical view of a portion of the shaft in FIG. 1 having flexible section deflection.
Figure 5:
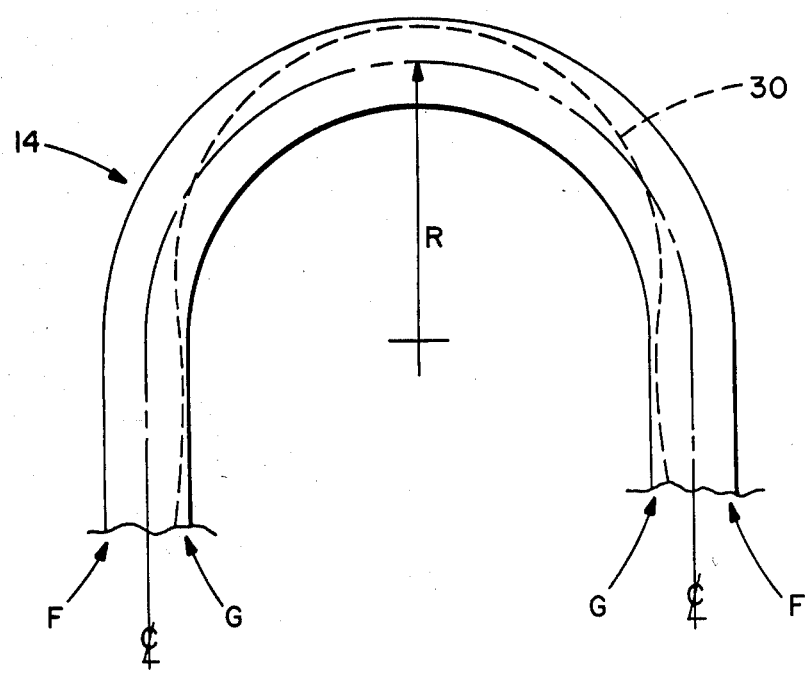
FIG. 5 is a diagrammatical side view of the flexible section of the instrument in FIG. 1 in a bent or deflected position showing a deflection channel in the core.

Referring now to FIGS. 4 and 5, the deflection compensation means will be described in further detail. FIG. 4 shows a diagrammatical view of a section of the shaft 8 located in the flexible section 14. In the embodiment shown, the cable 40 is contained in the conduit 30 of the core 28 and the shaft 8 is shown as being bent such as it would normally bend or flex to accommodate a channel or passageway to access a target area. Due to the bend of the shaft 8, the core 28 is preferably elastically deformed. The deformation of the core 28 is caused by a tensile force located generally in section F which causes the core 28 in section F to expand. In addition, the deformation of the core 28 is caused by a compressive force located generally in section G which causes the core 28 in section G to compress. The result of the expansion and compression is an elastic deformation or bend as shown.

Because the conduits 30, 32, 34 and 36 are formed by the core 28, the expansion and compression of the core 28 also affects the length and size of the conduits in the core. A conduit or conduit portion located in the expansion section F of the core will have an enlarged length in that section. A conduit or conduit portion located in the compression section G of the core will have a shortened length in that section. Although the cable 40 is generally flexible, it is not relatively elastic and cannot expand and contract to the same extent which the core 28 is capable of.

To better understand the present invention, a further description of the prior art is necessary. If a deflection means conduit was straight, as in the conduits of the prior art, a deflection means located in the conduit would have a tendency to involuntarily deflect the distal end of the instrument. This involuntarily deflection would be caused by the relatively non-elastic cable or wire of the deflection means retaining a relatively fixed length in the shaft except for manual control by the deflection control in the control head. Whereas, the conduits of the core would have a tendency to change their lengths due to expansion or compression of the core as the core is bent. A combination of a straight conduit with a varying length and a relatively fixed length deflection means would cause the distal end of the instrument to involuntarily or uncontrollably deflect as the shaft was passed through a bend in a channel or twisted after reaching a target area. Therefore, a deflection means could not be used in the prior art without involuntarily or uncontrollable deflection in the distal end of the instrument. Therefore, the non-straight, or in this embodiment, spiralled, path of the deflection conduit 30 has been provided by the present invention to prevent the involuntary or uncontrolled deflection of the distal end.

As shown in FIG. 4 the channel 30 and the deflection cable 40 are located in both the compressive section G and tensile section F at the bend in the shaft 8. The lengthening of the channel 30 along the expansion section F is compensated for by the shortening of the channel 30 along the compression section G to help maintain a substantially uniform overall length of the channel 30. Because of the substantially uniform or constant overall length of the channel 30 created by the non-straight channel path, the length of the cable 40 and the length of the conduit 30 remain relatively equal even when the shaft is bent or is located in a bending channel path and twisted or torqued in order to rotationally move the objective head 6. Since the length of the cable 40 and the length of the conduit 30 remain relatively equal there is no involuntary or uncontrolled deflection of the distal end of the instrument 2. Therefore, this deflection compensation means allows the use of a controllable distal end deflection means in a flexible core.

Referring to FIG. 5, a diagrammatic side view of a section of the flexible shaft 14 is shown with the deflection conduit 30. As described above, the deflection conduit 30 has a spiralled path about the longitudinal axis of the core 28. In a preferred embodiment, the number of full rotations of the conduit 30 along the length of the core 28 can be determined by an estimated critical bend. The critical bend is generally determined by the general intended use of the instrument 2. FIG. 5 shows the flexible shaft section 14 in one type of critical bend. This critical bend is then used to determine a length of the core 28 in the bend in which at least one full rotation would be needed to prevent uncontrolled deflection at the distal end. In the embodiment of the critical bend shown, the length of the core would be $\pi \times R$, where R is the radius of the bend and $\pi$ is approximately 3.14.

Once the critical bend length of the core 28 is calculated, the core can be fabricated such that there will be at least one full rotation of the deflection conduit 30 in the critical bend length. For example, if it is determined that the critical bend for a specific instrument would use one-fifth of the length of the core 28, then the core would have at least five full rotations of the deflection conduit 30 along its length. However, in alternative embodiments, the core 28 may have fewer or more rotations along its length.

As shown in FIG. 5, the core 28 is expanded along section F and compressed along section G. Because the conduit 30 is equally located in both sections F and G, the overall length of the conduit 30 remains relatively constant. Although the conduit 30 expands or lengthens in section G, the conduit 30 shortens in section F to thereby compensate for the bend or deflection of the flexible shaft 14 to retain a relatively constant conduit length. When the flexible section 14 is returned to a straight position the core 28 expands along section G and contracts along section F to retain the relatively constant length of the conduit 30. In an alternate embodiment, as stated above, the conduits can be spiralled or non-straight in the deflection section 12. In addition, although only conduit 30 has been described in regard to FIGS. 4 and 5, the deflection compensation means can be applied to all the conduits or selective conduits.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An instrument of a generally tubular flexible shape for accessing a target area, the instrument having a proximal region thereof, a distal region thereof, and a shaft therebetween, said shaft comprising:
   structural core means of a substantially flexible material with a first longitudinal axis and a first pre-determined length, said core means comprising a channel means at least partially offset from said first longitudinal axis and having a second pre-determined length; and
   deflection compensation means to compensate for channel means deformation in said core caused by shaft deflection.

2. An instrument as in claim 1 wherein said core means is an extruded polymer material.

3. An instrument as in claim 1 wherein said channel means is offset from said first longitudinal axis proximate said distal region.

4. An instrument as in claim 1 wherein said compensation means comprises said channel means being at least partially spiralled about said first longitudinal axis.

5. An instrument as in claim 1 wherein said compensation means comprises said channel means being non-straight relative to said first longitudinal axis and having a first cross-sectional position on said core at a first longitudinal position and a second cross-sectional position on said core at a second longitudinal position.

6. An instrument as in claim 1 wherein said channel means second pre-determined length is relatively longer than said core first pre-determined length.

7. An instrument as in claim 1 wherein said core means is twisted along at least a portion of said first longitudinal axis.

8. An instrument as in claim 7 further comprising a twist retention means.

9. An instrument as in claim 1 further comprising bundles of light transmitting fibers located with said conduit means.

10. An instrument as in claim 1 further comprising distal end deflection means.

11. An instrument as in claim 1 further comprising shaft torque stabilizer means.

12. An instrument as in claim 11 wherein said shaft torque stabilizer means is selectively connected to said core means.

13. An instrument as in claim 1 wherein said shaft is about 10 French in circumference.

14. A method of manufacturing a core for use in an instrument of a generally tubular flexible shape for accessing a target area, the method comprising the steps of:
   forming a flexible structural core of a resilient material having a first longitudinal axis and a first pre-determined length, said core comprising a first channel means at least partially offset from said first longitudinal axis; and
   twisting said core about said first longitudinal axis to thereby spiral said first channel means.

15. A method as in claim 14 wherein said channel means is spiralled about said first longitudinal axis.

16. A method as in claim 14 wherein said channel means has a second pre-determined length relatively shorter than said first pre-determined length after said step of twisting.

17. A method as in claim 14 further comprising the step of connecting a shaft torque stabilizer means to said core.

18. A method of manufacturing a shaft for use in an instrument of a generally tubular flexible shape for accessing a target area, the method comprising the steps of:
   forming a flexible structural core of a resilient material having a first longitudinal axis and a first pre-determined length, said core comprising a first channel means at least partially offset from said first longitudinal axis and having a first cross-sectional position on said core at a first longitudinal position and a second cross-sectional position on said core at a second longitudinal position; and
   positioning a distal end deflection means in said channel means.

* * * * *